(12) United States Patent
Tittelbach et al.

(10) Patent No.: US 11,752,330 B2
(45) Date of Patent: Sep. 12, 2023

(54) ELECTRODE BODY OF AN ELECTRODE ASSEMBLY AND ELECTRODE ASSEMBLY FOR ELECTRICAL STIMULATION, AND METHOD FOR PRODUCING AN ELECTRODE ASSEMBLY

(71) Applicant: PRECISIS AG, Heidelberg (DE)

(72) Inventors: Michael Tittelbach, Heidelberg (DE); Angela Liedler, Starnberg (DE); Gregor Remmert, Heidelberg (DE); Lasse Jagschies, Heidelberg (DE); Thorsten Göttsche, Rheinfelden (DE); Maik Gräfe, Rheinfelden (DE)

(73) Assignee: PRECISIS AG, Heidelberg (DE)

( * ) Notice: Subject to any disclaimer, the term of this patent is extended or adjusted under 35 U.S.C. 154(b) by 270 days.

(21) Appl. No.: 17/050,668

(22) PCT Filed: Apr. 11, 2019

(86) PCT No.: PCT/EP2019/059278
§ 371 (c)(1),
(2) Date: Oct. 26, 2020

(87) PCT Pub. No.: WO2019/206664
PCT Pub. Date: Oct. 31, 2019

(65) Prior Publication Data
US 2021/0236807 A1   Aug. 5, 2021

(30) Foreign Application Priority Data
Apr. 27, 2018   (DE) ..................... 10 2018 110 239.9

(51) Int. Cl.
*A61N 1/05*     (2006.01)
*A61N 1/20*     (2006.01)
(Continued)

(52) U.S. Cl.
CPC .......... *A61N 1/0539* (2013.01); *A61N 1/0502* (2013.01); *A61N 1/20* (2013.01); *A61N 1/3605* (2013.01); *H01B 5/14* (2013.01)

(58) Field of Classification Search
CPC .. A61N 1/0492; A61N 1/0526; A61N 1/0531; A61N 1/0534
See application file for complete search history.

(56) References Cited

U.S. PATENT DOCUMENTS 10,201,707 B2 * 2/2019 Hartig ................ A61N 1/36185
10,617,361 B2 * 4/2020 Hirata .................. A61N 1/0531
(Continued)

FOREIGN PATENT DOCUMENTS

DE   10 2014 108 315 A1   12/2015
DE   10 2015 113 420 A1    2/2017
(Continued)

*Primary Examiner* — Allen Porter
(74) *Attorney, Agent, or Firm* — WC&F IP (57) ABSTRACT

The invention relates to an electrode body (20) of an electrode assembly for electrically stimulating tissue of a living being, more particularly for neurostimulation. The electrode body (20) is designed to be arranged at a point between the skull and the scalp of a living being. The electrode body (20) has a stimulation surface, which is designed to be brought into contact with the tissue of the living being in order to produce an electrical stimulation of the tissue by alternating-current pulses and/or direct-current pulses. The electrode body (20) has a stimulation surface having an area of at least 50 mm², a stimulation surface having an area of at least 20 mm² and additionally a surface treatment which enlarges the effective stimulation surface, a fastening, structure for fastening the electrode body (20) to the tissue of a living being, a conductor connection point, by means of which the electrode body (20) can be connected, by soldering, adhesive bonding, welding or another connection technique, to an electrical conductor (4) for electrically (Continued)

connecting the electrode body (20) to an electrical device or another electrode body (20). Except for the stimulation surface, the electrode body (20) is completely surrounded by an electrically insulating carrier material (6), author the electrode body (20) has cut-outs (16) distributed over the circumference for fastening the electrode body (20) in a carrier material (6). The invention further relates to electrode assemblies and to a method for producing an electrode assembly.

9 Claims, 8 Drawing Sheets

(51) Int. Cl.
*A61N 1/36* (2006.01)
*H01B 5/14* (2006.01)

(56) References Cited

U.S. PATENT DOCUMENTS

| | | | |
|---|---|---|---|
| 11,395,917 B2* | 7/2022 | Liedler | A61N 1/0551 |
| 2008/0039895 A1* | 2/2008 | Fowler | A61N 2/006 |
| | | | 607/2 |
| 2008/0147146 A1* | 6/2008 | Wahlgren | A61B 5/24 |
| | | | 607/61 |
| 2008/0255582 A1* | 10/2008 | Harris | A61N 1/0526 |
| | | | 606/129 |
| 2009/0292336 A1* | 11/2009 | Nishida | A61N 1/3787 |
| | | | 607/45 |
| 2011/0137381 A1* | 6/2011 | Lee | A61N 1/36025 |
| | | | 607/62 |
| 2012/0245529 A1* | 9/2012 | Hummen | A61M 25/02 |
| | | | 604/175 |
| 2013/0060115 A1* | 3/2013 | Gehman | A61B 5/274 |
| | | | 600/372 |
| 2013/0268038 A1* | 10/2013 | Bikson | A61N 1/0472 |
| | | | 607/116 |
| 2015/0119898 A1* | 4/2015 | Desalles | A61N 1/0504 |
| | | | 607/116 |
| 2015/0148864 A1 | 5/2015 | Peterson et al. | |
| 2017/0095656 A1* | 4/2017 | Perraud | A61N 1/0476 |
| 2017/0333696 A1* | 11/2017 | Shibata | A61N 1/0476 |
| 2018/0132790 A1* | 5/2018 | Yao | A61B 5/6846 |
| 2018/0280694 A1* | 10/2018 | Mashiach | A61N 1/3756 |
| 2019/0053730 A1* | 2/2019 | Williams | A61N 1/0539 |

FOREIGN PATENT DOCUMENTS

| | | |
|---|---|---|
| EP | 0 682 496 B1 | 8/2000 |
| EP | 2038004 B1 | 1/2018 |
| WO | 2005002665 A2 | 1/2005 |
| WO | 201215883 A1 | 11/2012 |
| WO | 2018072894 A1 | 4/2018 |

* cited by examiner

ELECTRODE BODY OF AN ELECTRODE ASSEMBLY AND ELECTRODE ASSEMBLY FOR ELECTRICAL STIMULATION, AND METHOD FOR PRODUCING AN ELECTRODE ASSEMBLY

The invention relates to an electrode body of an electrode assembly for electrical stimulation of tissue of a living being, more particularly for neurostimulation. The invention further relates to an electrode assembly for electrical stimulation of tissue of a living being, more particularly for neurostimulation. The invention further relates to a method for producing an electrode assembly for electrical stimulation of tissue of a living being.

Such electrode bodies and electrode assemblies generate an electrical field in the region of tissue of a living being, in order to electrically stimulate this tissue, wherein the electrodes are fed by an energy source. The terms electrode and electrode body are essentially equivalent, wherein the term electrode body is used more particularly hereinbelow to describe the layout and the structure of such electrodes of an electrode assembly.

EP 2 709 716 A1 discloses a device for implantation in or on a head, wherein the device has a housing in which several electrodes are arranged, wherein the electrodes generate an electrical field in a defined region of the head. The device is configured to receive and transmit data by W-LAN.

WO 2005/002665 A2 discloses an electrode system designed for implantation in a human and having two rows of electrodes, wherein, in one row of electrodes, several electrodes are arranged next to one another on a line. The rows of electrodes can be actuated with different voltages, wherein an electrical field is generated.

EP 2 038 004 B1 discloses an electrode system designed for implantation on the head outside the skull and having several disk electrodes, wherein the disk electrodes are arranged in a matrix. Depending on the particular use, selected disk electrodes can be actuated by a switching subsystem in order to generate a desired electrical field, without having to change the position of the disk electrodes.

Proceeding from this, the object of the present invention is to make available an improved electrode body of an electrode assembly and to make available an improved electrode assembly. It is also the object of the present invention to make available an improved method for producing an electrode assembly.

The object is achieved by the electrode body having the features of claim 1. Advantageous embodiments are described in the dependent claims.

Accordingly, an electrode body of an electrode assembly for electrical stimulation of tissue of a living being, more particularly for neurostimulation, is provided. The electrode body is designed to be arranged at a location between the skull and the scalp of a living being. The electrode body has a stimulation surface, which is designed to be brought into contact with the tissue of the living being in order to generate an electrical stimulation of the tissue by alternating-current pulses and/or direct-current pulses. This also includes combined or superposed alternating-current pulses and direct-current pulses, for example also asymmetrical pulses, which do not have the same instantaneous or integral current flow in a positive and negative direction.

The electrode body can have a stimulation surface having a surface area of at least 50 $mm^2$. The electrical field generated by the electrode body of an electrode assembly is attenuated by the skull of the living being. By virtue of the fact that the electrode body has a stimulation surface measuring at least 50 $mm^2$ and generates a sufficiently strong electrical field without damaging the stimulation surface by electrochemical processes, this attenuation by the skull can be better compensated. Moreover, the stimulation surface of at least 50 $mm^2$ proves advantageous if electrical pulses with a long pulse duration are used since, with a constant current intensity, these lead to lower current densities at the stimulation surface, and irreversible electrochemical processes are therefore reduced. In addition, the brain surface that can potentially be stimulated is increased. The comparatively large stimulation surface also has a favorable effect on the signal-to-noise ratio.

Alternatively or additionally, the electrode body can have a stimulation surface with a surface area of at least 20 $mm^2$ and, additionally, a surface treatment that increases the effective stimulation surface. For example, with such a surface treatment, it is possible to obtain a rougher or pimpled surface or also a fractal surface, as a result of which a surface increase is achieved, and the transition impedance between electrode body and tissue is reduced, and therefore the signal-to-noise ratio is improved.

Alternatively or additionally, the electrode body can have a fixing structure for fixing the electrode body to the tissue of a living being.

Alternatively or additionally, the electrode body can have a conductor connection point, via which the electrode body can be connected, by soldering, adhesive bonding, welding or another connection technique, to an electrical conductor for electrically connecting the electrode body to an electrical device or to another electrode body.

Alternatively or additionally, the electrode body, except for the stimulation surface, can be completely surrounded by an electrically insulating carrier material. This permits simple arrangement and fixing of the electrode body in a higher-order structure, more particularly an electrode assembly. Moreover, the occurrence of leakage currents and short-circuit currents is prevented or at least reduced by the electrically insulating carrier material. Here, the electrode body can also be surrounded by a plurality of electrically insulating carrier materials. For example, a polyimide substrate can be applied to the electrode body, which polyimide substrate is additionally embedded in silicone.

Alternatively or additionally, the electrode body can have recesses distributed over a perimeter area of the body, for fixing the electrode body in a carrier material. Such recesses have the advantage that the electrode body can be better held in a fixed position in the carrier material, since an improved form-fit connection can be achieved. During production, the initially liquid carrier material, for example a silicone, enters the recesses of the electrode body and, after the carrier material has hardened, the electrode body is rigidly connected to the carrier material. The recesses can be arranged, for example, in a ring shape around a fastening opening of the electrode body and/or along the electrode edge.

In a particularly expedient embodiment, the carrier material has a first at least partially circumferential sealing lip on an exposed contacting side of the electrode body. A circumferential sealing lip has the advantage that the electrode body is protected against undesired interactions with the environment at the implantation site, wherein the circumferential sealing lip provides an insulation which remains intact even upon deformation of the electrode body or of an electrode assembly receiving the electrode body. In contrast to electrode bodies and electrode assemblies known from the prior art, the durability can thus be improved, and short circuits through electrolytes or tissue, located between electrode and skull, can be prevented or at least greatly reduced.

Moreover, the signal-to-noise ratio is improved. It is conceivable that the first circumferential sealing lip can be formed in one piece from the carrier material.

It is advantageous if the first at least partially circumferential sealing lip protrudes beyond the electrode body by 0.05 mm to 1 mm, more particularly by 0.1 mm to 0.3 mm. It has been found that these dimensions ensure the flexibility of the electrode body and of an electrode assembly receiving the electrode body and at the same time provide efficient insulation of the electrode body from external influences. The sealing lip can protrude beyond the electrode body in each spatial direction. For example, the sealing lip can protrude beyond the electrode body in the normal direction of the stimulation surface and/or centripetally to the stimulation surface.

According to an advantageous embodiment, the electrode body is circular, elliptic, annular or bean-shaped. Such a shape permits a good bearing of the electrode body on the tissue of the living being.

It is expedient if the conductor connection point of the electrode body is designed as a tangential conductor connection point. A tangential conductor connection point runs orthogonal to the connecting line between contact point and center point of the electrode body. A conductor attachable to the electrode body via the conductor connection point makes contact with the electrode body as a tangent. This has the advantage that, when the electrical conductor is subjected to mechanical loading, for example by a tensile force, the connection site is free of the load, and so there is less chance of the connection site being damaged and of the electrode thus failing. The electrical conductor can be welded or soldered onto the electrode body, for example.

However, it is also conceivable that the conductor connection point of the electrode body is designed as a right-angled conductor connection point. A right-angled conductor connection point is understood to mean a conductor connection point that perpendicularly intersects the contour line or circumferential line of the electrode body in the attachment region, such that a right angle forms between the conductor and the contour line or circumferential line in the attachment region. Compared to the tangential conductor connection point, the right-angled conductor connection point runs parallel, not orthogonal, to the connecting line between contact point and center point of the electrode body. This shape of the conductor connection point is advantageous for example in the case of polyimide substrates.

In an advantageous embodiment, an electrical conductor for electrically connecting the electrode body to an electrical device or to another electrode body is connected at the conductor connection point.

It is advantageous if the electrical conductor has a meandering course. A meandering arrangement reduces the loading of the electrical conductor, more particularly in its attachment region, which loading may arise, for example, through bending and pulling of an electrode assembly that receives the electrode. The load relief is further improved by arranging the conductor on a curved path. Advantageously, the curved path extends over an angle range of 40° to 100°, based on a 360° system, about the primary electrode.

According to an expedient embodiment, the connection site of the electrical conductor to the electrode body is sealed off, more particularly sealed off with an epoxy resin. This has the advantage that the sensitive connection site is protected from external influences, for example liquids, which would lead to failure of the electrode, for example through corrosion.

In an advantageous embodiment, the electrical conductor is made from a material or a material composition which, in ion-containing solution, does not form an electrochemical local element with the material of the electrode body. By such a choice of material, the likelihood of corrosive processes leading to damage of the electrode or of the electrical conductor is reduced.

Advantageously, the electrode body or at least the stimulation surface is made wholly or partially from a biocompatible and inert material, for example platinum-iridium, which, inherently or through a special coating, for example with iridium oxide or graphene, has a high charge injection capacity.

It is advantageous if the fixing structure of the electrode body has an insulating material sleeve, which is designed to insulate a mechanical fastening element from the electrode body. The insulating material sleeve thus provides electrical insulation of a mechanical fastening element, for example a screw, such that no undesired electrical currents from the electrode body to the fastening element are generated.

The fixing structure of the electrode body can have fixing means at the circumference or at an end of the electrode body or also fixing means embedded in the carrier material next to or adjoining the electrode body, in order to connect the electrode body to the tissue of a living being.

In an expedient embodiment, the fixing structure has at least one fastening opening in the electrode body, through which fastening opening the electrode body can be fastened by the mechanical fastening element, e.g. a screw, a nail, a clip, a thread or a similar mechanical fastening element, to the tissue of the living being. Moreover, it is particularly advantageous if the insulating material sleeve described above is arranged in the fastening opening. By way of the fastening opening, the electrode body can then be fastened to a bone structure, for example, of the living being, by means of a mechanical fastening element, for example a screw, being guided through the fastening opening, particularly advantageously through an insulating material sleeve arranged in the fastening opening, and being fixed to the bone structure. However, other fastening means are also conceivable, such as surgical threads, for fastening the electrode body. In this case, the fastening opening, advantageously also an insulating material sleeve arranged in the fastening opening, is designed such that fastening of the alternative fastening means is possible. For example, in the case of the surgical thread, the insulating material sleeve has at least two openings.

According to an advantageous embodiment, the insulating material sleeve has a second at least partially circumferential sealing lip. This has the advantage that the electrode body is protected from liquids that can get into the electrode body through gaps between the electrode body, or the electrode assembly receiving the electrode body, and the insulating material sleeve. It is conceivable that the insulating material sleeve or the second circumferential sealing lip can be formed in one piece from the carrier material.

It is advantageous if the insulating material sleeve is made at least partially from a polyether ether ketone (PEEK). Polyether ether ketone is a thermoplastic resistant to high temperatures and also used in medical technology. Polyether ether ketone has the advantage of being biocompatible and radioparent. Moreover, the material has a low coefficient of friction, such that only a slight force can be transmitted from a fastening means, such as a screw, to the insulating material sleeve and thus to the electrode body, and the latter is thus protected against damage, for example deformation. Polyether ether ketone also has an electrically insulating effect, such that no undesired electrical currents can flow between the electrode body and the mechanical fastening means.

According to an advantageous embodiment of the invention, the electrode body has a preformed concave stimulation surface. Such a stimulation surface can conform optimally to the outer shape of most skull regions of a living being. The electrode body is thus better adapted to the curvature of the bone structure.

Alternatively, the electrode body can have a preformed flat stimulation surface with at least one incision and/or a cutout, by which a flexible adaptability of the electrode body to the outer contour of the skull of a living being is improved.

It is expedient if the electrode body is additionally suitable for detecting bioelectric signals of the living being. For example, an electroencephalogram (EEG) or electrocardiogram (ECG) or electromyogram (EMG) can be recorded with the aid of the electrode body. To this end, an amplifier with analog-digital converter (ADC) and, if appropriate, an analog or digital signal filter can be connected to the electrode body or integrated in the latter and, after detection of bioelectric signals of the living being, can be used for diagnostic purposes or for controlling the stimulation. Moreover, for this purpose, an evaluation and control unit can be connected to the electrode body or can be integrated in an energy source attachable to the electrode body.

In an advantageous embodiment, the electrode body has a surface area of at most 7.1 cm$^2$, more particularly a surface area of at most 4.6 cm$^2$. A comparatively small electrode body of this kind permits good integration and reduced intervention in the tissue of the living being, such that the risk of tissue damage is reduced.

According to an advantageous embodiment, the electrode body has a thickness of at most 2 mm, more particularly a thickness of at most 1 mm. In this way, an assembly formed with one or more electrode bodies can likewise have a small thickness, for example less than 3 mm, less than 2 mm or less than 1 mm. In this way, an implanted electrode assembly barely protrudes from under the scalp of the living being. This has a cosmetic advantage, since others cannot see any sign of the implanted electrode assembly. Moreover, the chance of damage by external influences is reduced, since the potential surface area for such damage is smaller. A smaller thickness also improves the wearing comfort for the living being.

The object is moreover achieved by an electrode assembly having the features of claim 20. Advantageous embodiments are described in the dependent claims.

Thus, an electrode assembly is provided for electrical stimulation of tissue of a living being, more particularly an electrode assembly for neurostimulation, having at least one primary electrode and at least one secondary electrode. One, several or all of the primary electrodes are each formed by an electrode body, and/or one, several or all of the secondary electrodes are each formed by an electrode body.

The at least one primary electrode and the at least one secondary electrode are each connected by means of electrical conductors to an attachment element, wherein the attachment element is configured for connection to another electrode or an energy source. Alternatively or additionally, the primary electrode and the secondary electrode are arranged on a common carrier material.

The electrodes of the electrode assembly are connected to an attachment element, wherein the attachment element can be connected to an energy source and/or to an electrical signal source in order to supply the electrodes with current. The electrical signal source can be designed to transmit electrical stimulation signals. The electrodes can in this case be embedded in the carrier material. The attachment element can have a plug connector or be designed as a plug connector. However, it is also conceivable that the attachment element is designed as a polyether ether ketone adapter, which constitutes the transition between the electrode assembly and the energy source or the electrical signal source. The energy source and/or the signal source can be implanted in the body of the living being at a different position than the electrode assembly, wherein the energy source is connected to the attachment element by means of an electrical conductor, and this electrical conductor can be welded or soldered to the attachment element.

The object is further achieved by an electrode assembly having the features of claim 21. Advantageous embodiments are described in the dependent claims.

Thus, an electrode assembly for electrical stimulation of tissue of a living being, more particularly for neurostimulation, is provided, wherein the electrode assembly is designed to be arranged at a location between the skull and the scalp of a living being. The electrode assembly has at least one primary electrode and at least one secondary electrode. It moreover has a stimulation surface, which is designed to be brought into contact with the tissue of the living being in order to generate an electrical stimulation of the tissue by alternating-current pulses and/or direct-current pulses. This also includes combined or superposed alternating-current and direct-current pulses, for example also asymmetrical pulses, which do not have the same instantaneous or integral current flow in a positive and negative direction.

The electrode assembly according to the invention can be designed to be implanted between the scalp and skull of the living being. Specifically in the field of neurostimulation for epilepsy patients in whom treatment with medication does not work, a maximally invasive method has hitherto often been applied in which an intracranial electrode system is implanted in order to alleviate the patient's symptoms. The electrode assembly according to the invention can be implanted on the cranial bone of the living being in order to achieve the necessary stimulation of defined regions of the brain, and this represents a much less invasive intervention for the patient and thus places less strain on the latter.

The electrode assembly can have an overall size of the stimulation surface of the primary electrodes and/or an overall size of the stimulation surface of all the secondary electrodes having a surface area of at least 50 mm$^2$. The electrical field generated by the electrode assembly is attenuated by the skull of the living being. By virtue of the fact that the electrode assembly has a stimulation surface measuring at least 50 mm$^2$ and generates a sufficiently strong electrical field without damaging the stimulation surface by electrochemical processes, this attenuation by the skull can be better compensated. Moreover, the stimulation surface of at least 50 mm$^2$ proves advantageous if electrical pulses with a long pulse duration are used since, with a constant current intensity, these lead to lower current densities at the stimulation surface, and irreversible electrochemical processes are therefore reduced. In addition, the brain surface that can potentially be stimulated is increased. The comparatively large stimulation surface also has a favorable effect on the signal-to-noise ratio. The electrode surface area is limited in the upward direction by the overall size of the electrode assembly, in order still to be able to implant the electrode assembly in humans.

Alternatively or additionally, the electrode assembly can have an overall size of the stimulation surface of the primary electrodes and/or an overall size of the stimulation surface of all the secondary electrodes having a surface area of at least 20 mm$^2$ and, additionally, a surface treatment that enlarges the effective stimulation surface. For example, with such a surface treatment, it is possible to obtain a rougher or pimpled surface or also a fractal surface, as a result of which a surface increase is achieved, and the transition impedance between electrode body and tissue is reduced, and therefore the signal-to-noise ratio is improved.

Alternatively or additionally, the electrode assembly has a fixing structure for fixing the electrode assembly to the tissue of a living being.

Alternatively or additionally, the electrode assembly, except for the stimulation surfaces of the primary and secondary electrodes, is completely surrounded by an electrically insulating carrier material. This permits simple arrangement and fixing of the electrode assembly on the tissue of the living being. Moreover, the occurrence of leakage currents and short-circuit currents on the electrodes is prevented or at least reduced by the electrically insulating carrier material. Here, the electrode assembly can also be surrounded by a plurality of electrically insulating carrier materials. For example, a polyimide substrate can be applied to the primary and/or secondary electrodes, which polyimide substrate is additionally embedded in silicone.

In an advantageous embodiment of the electrode assembly, a reinforcing element, more particularly a reinforcing net, is arranged on the carrier material. The tear resistance of the electrode assembly can be increased by means of such a reinforcing element. This has the advantage that the geometric precision of the electrode assembly, i.e. the position of the primary electrode and of the secondary electrodes relative to each other, and thus the necessary electrical field can be ensured. Advantageously, the reinforcing element is a reinforcing net, for example a surgical net, of which the strands extend between the primary electrode and the secondary electrodes. It is possible that certain parts of the electrode assembly have no reinforcing element. For example, it is conceivable that no such reinforcing element is arranged on the contacting portion of the electrode assembly, so as not to reduce its flexibility.

According to an advantageous embodiment of the electrode assembly, at least one electrical conductor is at least partially surrounded by the carrier material. This has the advantage that the electrical conductor is maintained in its position on the carrier material. This avoids undesired shifting of the electrical conductor. Moreover, the electrical conductor is insulated from external influences, such that it is screened off from liquids, for example, and an undesired reaction is thus prevented. It is expedient if the thickness of the electrode assembly is smaller than 4 mm, more particularly smaller than 2 mm. In this way, an implanted electrode assembly barely protrudes from under the scalp of the living being. This has a cosmetic advantage, since others cannot see any sign of the implanted electrode assembly. Moreover, the chance of damage by external influences is reduced, since the potential surface area for such damage is smaller. A smaller thickness also improves the wearing comfort for the living being.

According to an advantageous embodiment, the electrode assembly has at least one primary electrode and at least two secondary electrodes. It is particularly advantageous if the electrode assembly has at least four secondary electrodes. A greater number of electrodes permits more precise control of the electrical field configuration, which may be advantageous, for example, on account of inhomogeneity in the conductivity of the tissue, or for more precise focusing of the electrical field onto one tissue region. Moreover, with a plurality of electrodes, it is possible to choose between a plurality of channels of a signal lead, which increases the information content. It is advantageous if the electrode assembly has between three and eight secondary electrodes, in particular precisely four secondary electrodes.

It is advantageous if at least one of the electrical conductors of the secondary electrodes is arranged in a meandering shape around the primary electrode, wherein the meandering arrangement of the electrical conductor runs along a curved path around the primary electrode. A meandering arrangement reduces the mechanical loading of the electrical conductors, more particularly of their attachment regions, which loading may arise, for example, through bending and pulling the electrode assembly. The load relief is further improved by the arrangement on a curved path. Advantageously, the curved path extends over an angle range of 40° to 100°, based on a 360° system, about the primary electrode.

In principle, the carrier material of the electrode assembly can have fastening structures with which the electrode assembly can be fastened to a bone structure of the living being. The fastening structures can be designed, for example, as screw holes or eyelets for producing a stitched connection.

Alternatively or in combination, the primary electrode and/or at least one of the secondary electrodes have at least one fastening opening, wherein an insulating material sleeve is arranged in each one of the fastening openings. By way of the fastening opening, the electrode assembly can then be fastened to a tissue structure of the living being, by means of fastening elements, for example screws, being guided through the insulating material sleeves arranged in the fastening openings, and being fixed to the tissue structure. However, other fastening means are also conceivable, such as surgical threads, for fastening the electrodes. In this case, the insulating material sleeve is designed such that fastening of the alternative fastening means is possible; for example, in the case of the surgical thread, through at least two openings in the insulating material sleeve. By the fastening via the primary electrode and/or the secondary electrodes, the remaining electrodes can at the same time be held at a desired position and an improved contact with the cranial bone can be achieved, such that the desired electrical field can also be generated at the desired site over the period of implantation of the electrode assembly. Fastening of this kind also avoids undesired tissue growth between electrode and cranial bone. Moreover, the insulating material sleeve provides an electrical insulation of the fastening means, such that no undesired electrical currents are generated from the primary electrode and/or the secondary electrodes to the fastening element.

The insulating material sleeve can be made at least partially from a polyether ether ketone (PEEK). Polyether ether ketone is a thermoplastic resistant to high temperatures and also used in medical technology. Polyether ether ketone has the advantage of being biocompatible and radioparent. Moreover, the material has a low coefficient of friction, such that only a slight force can be transmitted from the screw to the insulating material sleeve and thus to the respective electrode, and the latter is thus protected against damage, for example deformation. Polyether ether ketone also has an electrically insulating effect, such that no undesired electrical currents can flow between the electrodes and the screw.

The insulating material sleeve of the electrode assembly can have a second at least partially circumferential sealing lip. This has the advantage that the electrodes are protected from liquids that can get into the electrodes through gaps between the electrode assembly and the insulating material sleeve. It is conceivable that the insulating material sleeve or the second circumferential sealing lip can be formed in one piece from the carrier material.

Alternatively or in combination, the primary electrode and/or at least one of the secondary electrodes have recesses distributed over the perimeter, for fixing the electrode body in the carrier material. Such recesses have the advantage that the primary electrode and the secondary electrodes can be better fixed in the carrier material, since an improved form-fit connection can be achieved. During production, the initially liquid carrier material, for example a silicone, enters the recesses of the primary electrode and of the secondary electrodes and, after the carrier material has hardened, the primary electrode and the secondary electrodes are rigidly connected to the carrier material. The recesses can be arranged, for example, in a ring shape around the fastening opening of the primary electrode body and/or at least one of the secondary electrodes.

Alternatively or in combination, a connection site of the electrical conductor to the primary electrode and/or to at least one of the secondary electrodes is a tangential conductor connection point. A tangential conductor connection point runs orthogonal to the connecting line between contact point and center point of the respective electrode. The conductor makes contact with the electrode as a tangent. This has the advantage that, when the electrical conductor is subjected to loading, for example by a tensile force, the connection site is free of the load, and so there is less chance of the connection site being damaged and of the respective electrode thus failing. The electrical conductor can be welded or soldered onto the electrode body, for example.

However, it is also conceivable that a connection site of the electrical conductor to the primary electrode and/or to at least one of the secondary electrodes is designed as a right-angled conductor connection point. A right-angled conductor connection point is understood to mean a conductor connection point that perpendicularly intersects the contour line or circumferential line of the electrode body in the attachment region, such that a right angle forms between the conductor and the contour line or circumferential line in the attachment region. Compared to the tangential conductor connection point, the right-angled conductor connection point runs parallel, not orthogonal, to the connecting line between contact point and center point of the electrode. This shape of the conductor connection point is advantageous for example in the case of polyimide substrates.

In an expedient embodiment, the electrode assembly has a contacting portion, wherein the attachment element is arranged on the contacting portion, and wherein the contacting portion protrudes laterally from the electrode assembly. By means of the protruding contacting portion, the attachment element can be mechanically isolated from the region of the primary electrode and of the secondary electrode, such that undesired interactions are avoided.

It is moreover advantageous if the contacting portion has a greater length than width. The length is the dimension in the direction of protrusion of the contacting portion, wherein the width is the dimension transverse to the direction of protrusion of the contacting portion. By virtue of the elongate shape, forces acting on the contacting portion can be dissipated, such that these forces cannot reach the region of the electrodes and cannot cause damage there.

It is moreover advantageous if fastening elements for screw fastening are arranged on the contacting portion. The fastening elements can be designed, for example, as elongate holes, wherein the contacting portion can be fastened to the living being by means of screws or other fastening means. In this way, the contacting portion can be fastened securely to the living being, wherein mechanical forces can be dissipated via the skull. The fastening elements can be arranged in such a way that they form a six-point bearing, wherein the degrees of freedom in rotation and translation are limited.

According to an expedient embodiment, the total surface area of the secondary electrodes is greater than the surface area of the primary electrode. This embodiment permits good current distribution across the tissue surface of the living being and a reduced risk of tissue damage. Moreover, it is advantageous if the primary electrode and/or the secondary electrodes each have a surface area of 50 $mm^2$ to 71 $mm^2$, more particularly a surface area of 20 $mm^2$ to 46 $mm^2$. With these electrode surface areas, a particularly good current distribution is achieved, with reduced risk of tissue damage.

Alternatively, in an advantageous embodiment, the total surface area of the secondary electrodes can be smaller than the surface area of the primary electrode. This embodiment permits an inverted direction of the stimulation current such as anodal stimulation instead of a cathodal stimulation, without this leading to corrosion-induced damage of the electrodes. In this way, different indications and pathologies can be treated.

It is advantageous if the secondary electrodes are arranged on at least one circular path around the primary electrode. In a further advantageous embodiment, the secondary electrodes of the electrode assembly can be arranged equidistant on at least one circular path around the primary electrode. Moreover, it is expedient if the secondary electrodes are distributed on a concentric circular path around the primary electrode. This distribution of the secondary electrodes around the primary electrode additionally favors the generation of an electrical field through a screen, for example a skull cap.

According to an expedient embodiment, the center point of at least one of the secondary electrodes is arranged at a distance of 5 mm to 55 mm, more particularly at a distance of 10 mm to 50 mm, from the center point of the primary electrode. It is moreover advantageous if the edge of at least one of the secondary electrodes is arranged at a distance of 1 mm to 8 mm, more particularly at a distance of 2 mm to 6 mm, from the edge of the primary electrode. It has been found that short distances of the secondary electrodes from the primary electrode permit optimal focusing of the electrical field, wherein a sufficient distance of the secondary electrodes to the primary electrode means that the chance of a leakage current and short-circuit current can be reduced or prevented and the depth of penetration of the electrical field into the head can be increased. These distances thus constitute an optimized middle way between the conflicting requirements of the focusing and the leakage currents and short-circuit currents. A greater distance of the electrodes leads to a higher signal but also to lower focusing.

The carrier material advantageously has at least one clearance, wherein the clearance is arranged in each case between adjacent secondary electrodes. It is also conceivable that the carrier material has in parts a tapering, that is to say a decreasing or smaller material thickness. In this way, the electrode assembly can be designed to be flexible. The clearance or tapering increases the flexibility more particularly on the secondary electrodes, wherein a clearance or tapering is advantageously arranged between in each case two adjacent secondary electrodes. By virtue of the increased flexibility, it is possible to react to the irregular surface of the skull cap of a living being, since the electrode assembly has a sufficient contact with the skull cap at each position.

It is proposed that the carrier material has a first at least partially circumferential sealing lip on an exposed contacting side of the primary electrode and/or on at least one of the secondary electrodes. A circumferential sealing lip has the advantage that the electrodes are protected against undesired interactions with the environment at the implantation site, wherein the circumferential sealing lip provides an insulation which remains intact even upon deformation of the electrode assembly. In contrast to electrode assemblies known from the prior art, the durability can thus be improved, and short circuits through electrolytes or tissue, located between electrode and skull, can be prevented or at least greatly reduced. Moreover, the signal-to-noise ratio is improved. It is conceivable that the first circumferential sealing lip can be formed in one piece from the carrier material.

According to an advantageous embodiment, a first at least partially circumferential sealing lip protrudes at least partially beyond one, several or all of the primary electrodes and/or at least partially beyond one, several or all of the secondary electrodes by 0.05 mm to 1 mm, more particularly 0.1 mm to 0.3 mm. It has been found that these dimensions ensure the flexibility of the electrode assembly and at the same time provide efficient insulation of the electrodes from external influences. The sealing lip can protrude beyond the electrode body of the respective electrode in each spatial direction. For example, the sealing lip can protrude beyond the electrode body in the normal direction of the stimulation surface and/or centripetally to the stimulation surface.

Each insulation described in this application, for example through the carrier material or sealing lips, also contributes to an improved signal quality of the electrodes, such that the signal-to-noise ratio is improved.

The connection site of the electrical conductor to the primary electrode and/or at least one of the secondary electrodes can be sealed off, more particularly with an epoxy resin or another sealant. This has the advantage that the sensitive connection site is protected from external influences, for example liquids, which would lead to failure of the respective electrode, for example through corrosion.

Advantageously, the electrical conductor is made from a material which, if in contact with the electrode material, does not form an electrochemical local element in aqueous electrolyte solution. By such a choice of material, the likelihood of corrosive processes that lead to damage of the electrode or of the electrical conductor is reduced.

The object is moreover achieved by a method having the features of claim 38. Advantageous embodiments are described in the dependent claims.

Thus, a method is proposed for producing an electrode assembly for electrical stimulation of tissue of a living being, more particularly for producing an electrode assembly in accordance with the features described above.

In a method step a), electrode bodies are produced, e.g. by laser cutting or punching, from a film of an electrode material of suitable thickness. In a method step b), a surface coating and/or a structuring of the surface is optionally applied on at least one part of the electrode surface. In a method step c), an electrical conductor is mounted on each electrode body, or the electrical conductor is produced in one piece together with the electrodes. In a method step d), an epoxy resin or another electrical insulator is optionally applied to the connection site. In a method step e), a mold of the electrode assembly is cast from the carrier material. In a method step f), the electrode body and optionally the electrical conductor and optionally the reinforcing element are embedded. In a method step g), an electrical conductor is connected to the contacting portion of the electrode assembly.

The object is moreover achieved by a method having the features of claim 39. Advantageous embodiments are described in the dependent claims.

Thus, a method is proposed for producing an electrode assembly for electrical stimulation of tissue of a living being, more particularly for producing an electrode assembly in accordance with the features described above.

In a method step a), a carrier material is made available. In a method step b), one or more electrode bodies are generated on the carrier material by a chemical vapor deposition process and/or by electrolytic deposition. In a method step c), a surface coating and/or structuring of a surface is optionally applied on at least one part of the electrode surface. In a method step d), the carrier material is optionally embedded in a further insulating carrier material.

In an advantageous embodiment of the methods, at least one electrical conductor for electrically connecting the electrode body to an electrical device or to another electrode body is generated by a chemical vapor deposition process and/or by electrolytic deposition and is connected to the electrode body.

The invention is explained in more detail below by way of example and with reference to the appended drawings, in which.

Figure 1:
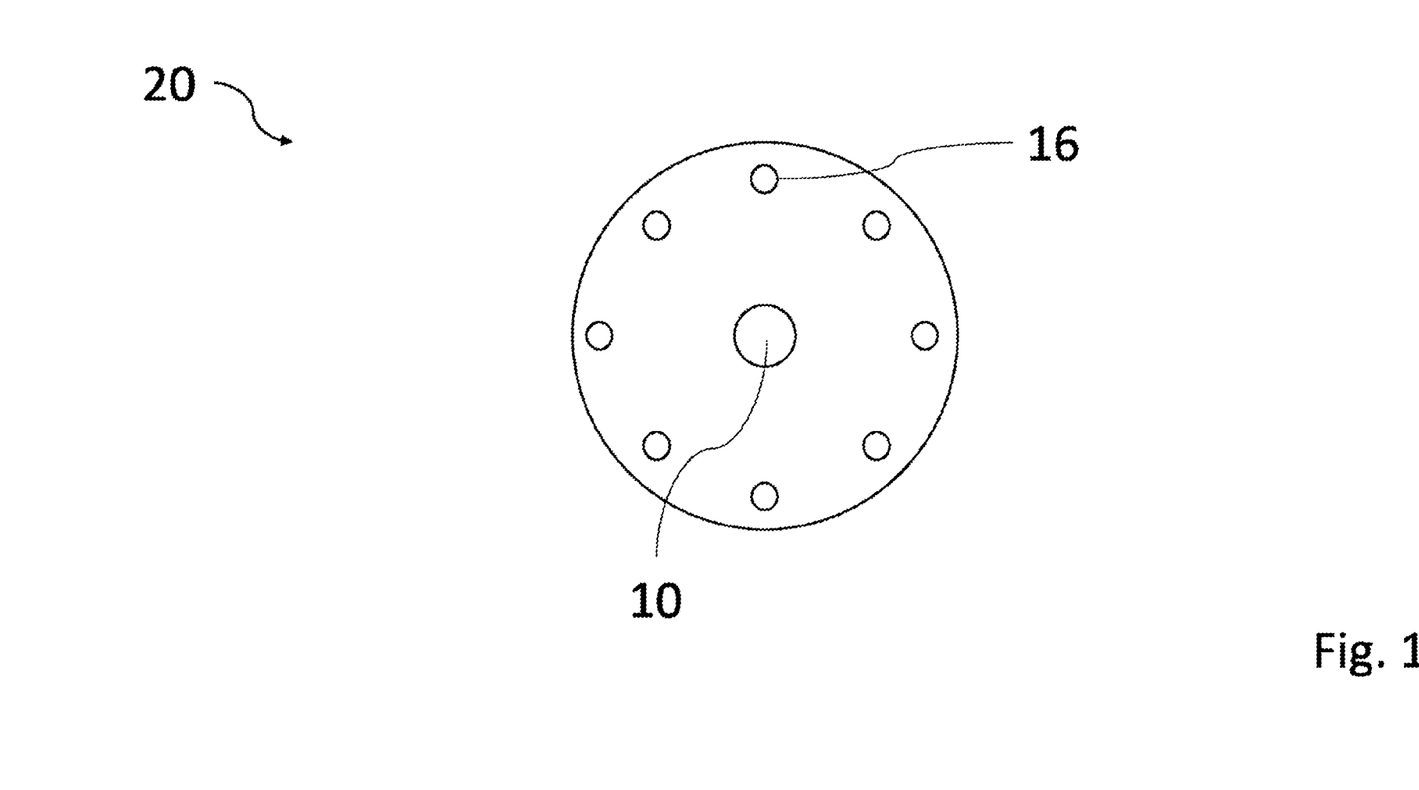
FIG. 1 shows a schematic layout of an electrode body.
Figure 3:
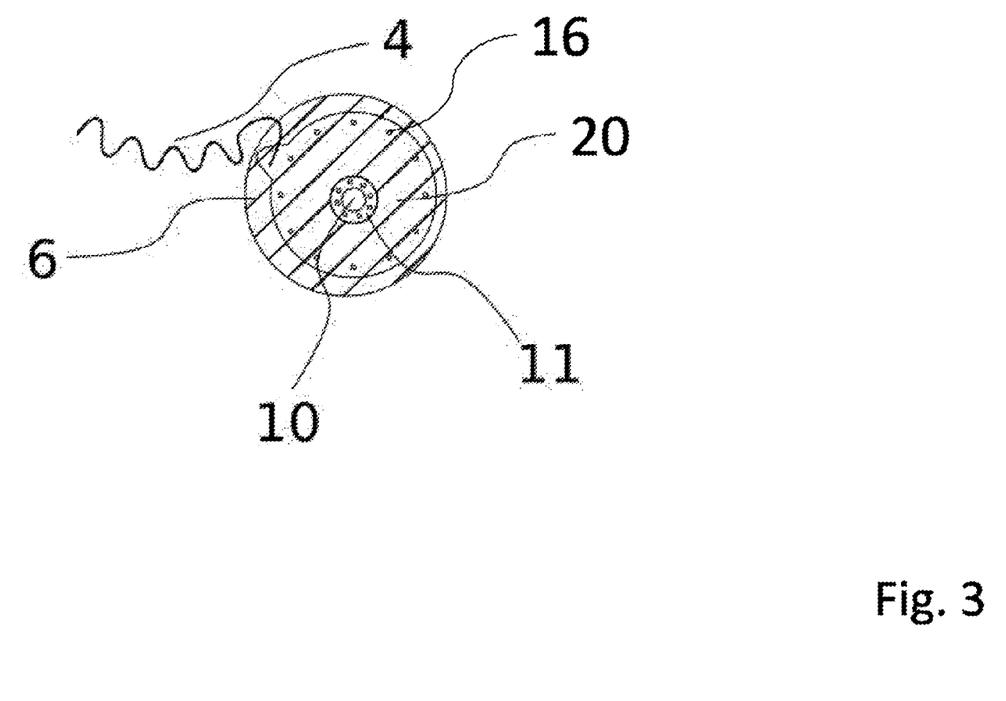
FIG. 3 shows a schematic illustration of the electrode body from FIG. 2 with a carrier material.

FIG. 1 shows a schematic layout of an electrode body 20. The electrode body 20 shown is designed here as a round electrode. However, other electrode shapes are also conceivable. It is clear that the electrode body 20 has a fastening opening 10 for fastening to a living being. It is also clear that the electrode body 20 has recesses 16 distributed over its perimeter area. Improved fixing of the electrode body 20 in a carrier material 6, shown for example in FIG. 3, is achieved through the recesses 16. In the production of an electrode assembly 1, shown for example in FIG. 6 and receiving the electrode body 20, the carrier material 6 is initially in a liquid state, wherein the carrier material 6 distributes itself in the recesses 16, and the electrode body 20 can thus be held in a fixed position after the carrier material 6 has hardened.

Figure 2:
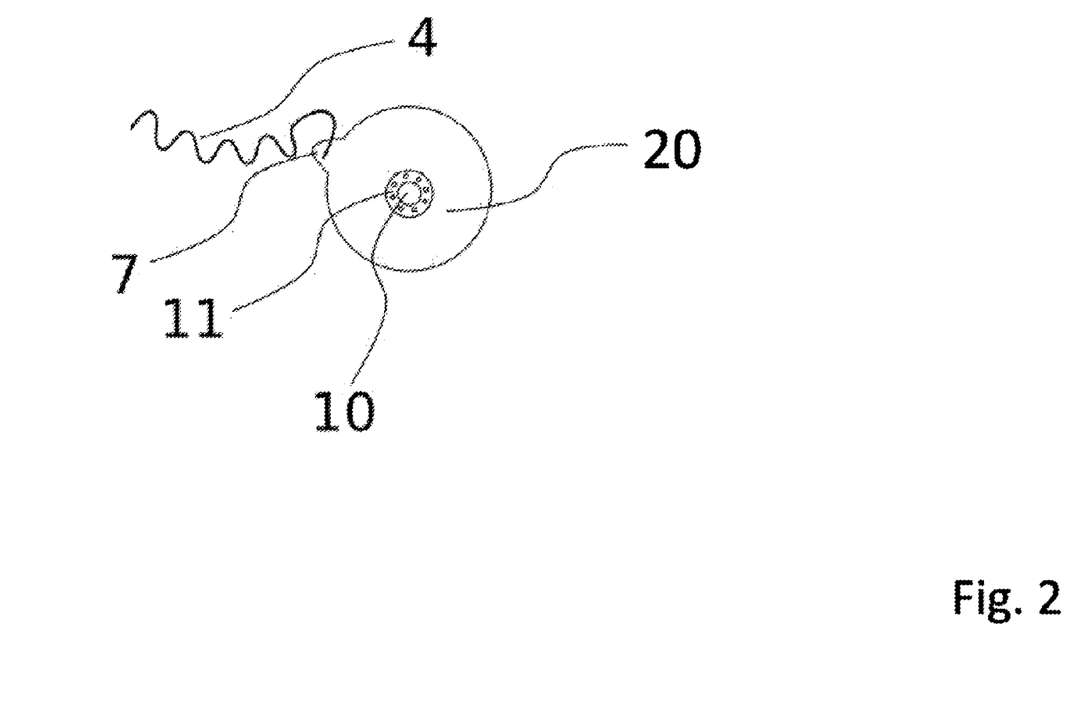
FIG. 2 shows a schematic illustration of an electrode body with an attached electrical conductor and an insulating material sleeve.

FIG. 2 shows a schematic illustration of an electrode body 20, likewise designed as a round electrode, with an attached electrical conductor 4. For attaching the electrical conductor 4, a conductor connection point 7 is provided on the electrode body 20, which conductor connection point 7 can be designed, for example, as a projection protruding from the circular surface of the round electrode, so as not to reduce the effective stimulation surface of the electrode body 20. In the present case, the conductor connection point 7 is designed as a tangential conductor connection point 7, such that the attached electrical conductor 4 contacts the electrode body 20 as a tangent. In this way, the connection point is relieved of any tensile force that arises, thereby avoiding damage to the conductor connection point 7 and consequent failure of the electrode. The electrical conductor 4 can be soldered or welded onto the conductor connection point 7 of the electrode body 20, it being advantageous if the connection site is sealed off from external influences, for example with an epoxy resin. It will be noted that the electrical conductor 4 has a meandering course. This reduces the loading of the electrical conductor 4, more particularly in the region of its attachment to the conductor connection point 7, which loading may arise, for example, through bending and pulling of an electrode assembly 1 receiving the electrode body.

It will also be noted that the electrode body 20 has a fastening opening 10 into which an insulating material sleeve 11 is inserted. In this way, the electrode body 20 can be fastened to a skull of the living being via a fastening element, for example a screw, through the insulating material sleeve 11. In doing this, the insulating material sleeve 11 prevents a situation in which an excessive torque is transmitted to the electrode body 20 and thus damages the latter. Moreover, an undesired current flow between the electrode body 20 and the fastening element is avoided. The insulating material sleeve 11 can be made, for example, from a polyether ether ketone. By fastening the electrode body 20 by way of a fastening opening 10, it is possible to ensure an exact position of the electrode body 20, which can generate a desired electrical field in the target region.

FIG. 3 shows the electrode body 20 from FIG. 2. It will be seen from this view that the electrode body 20 is embedded in a carrier material 6 indicated by hatching. The carrier material 6 is electrically insulating and completely surrounds the electrode body except for the stimulation surface. The carrier material 6 can be made of a silicone, for example. However, it is also conceivable to use other materials that satisfy the required properties (biocompatibility, flexibility, electrical insulation, etc.). The carrier material 6 allows the electrode body 20 to be easily arranged and fixed in a higher-order structure, more particularly an electrode assembly 1. Moreover, the occurrence of leakage currents and short-circuit currents is prevented or at least reduced by the electrically insulating carrier material 6.

Moreover, the electrode body 20 has recesses 16. The carrier material 6, initially in liquid form in a production process, penetrates into the recesses 16 and, after hardening, thus supports the fixing of the electrode body 20 in the carrier material 6.

Figure 4:
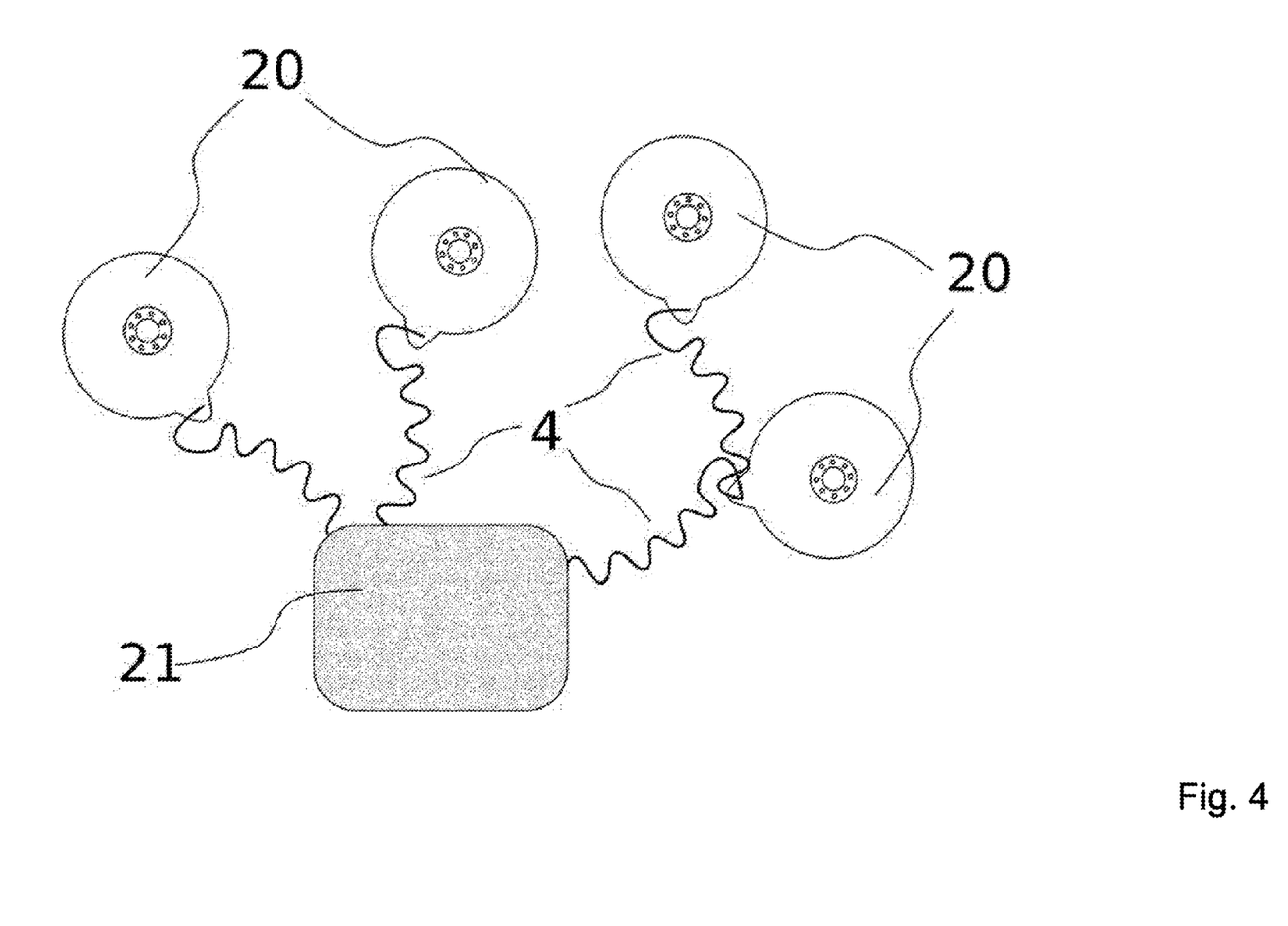
FIG. 4 shows a schematic illustration of several electrode bodies, which are connected to an energy source via electrical conductors.

FIG. 4 shows a schematic illustration of several electrode bodies 20, namely a total of four electrode bodies 20, which are connected via electrical conductors 4 to an energy source 21. The energy source 21 can be designed as a supply source, in order to supply the electrode bodies with electric current and thereby permit their operation. Alternatively or additionally, the energy source 21 can be designed as a signal source, in order specifically to generate electrical stimulation signals to the electrodes.

It will be noted that the electrode bodies 20 do not have to be connected directly to the energy source 21. An arrangement is equally conceivable in which an electrode body 20 is connected to a further electrode body 20, which is in turn attached to the energy source 21. For this purpose, the respective electrical conductor 4 runs either between an electrode body 20 and the energy source 21 or between two electrode bodies 20. By connecting an electrode body 20 to the energy source 21 indirectly via a further electrode body 20, it is also possible to reach tissue regions farther away from the energy source, without having to keep a stock of longer electrical conductors 4 or having to stretch these, thereby exposing them to a higher risk of loading. Of course, it is also possible for several electrode bodies, i.e. more than two electrode bodies, to be connected to a further electrode body 20. At the conductor connection point 7 provided for connection of the electrical conductors 4, the several conductors 4 can for example be soldered on next to each other. In principle, it is of course also conceivable to use a longer conductor 4 for the more distant electrode body 20 and to electrically connect up another and nearer electrode body 20 as a branch.

Figure 5:
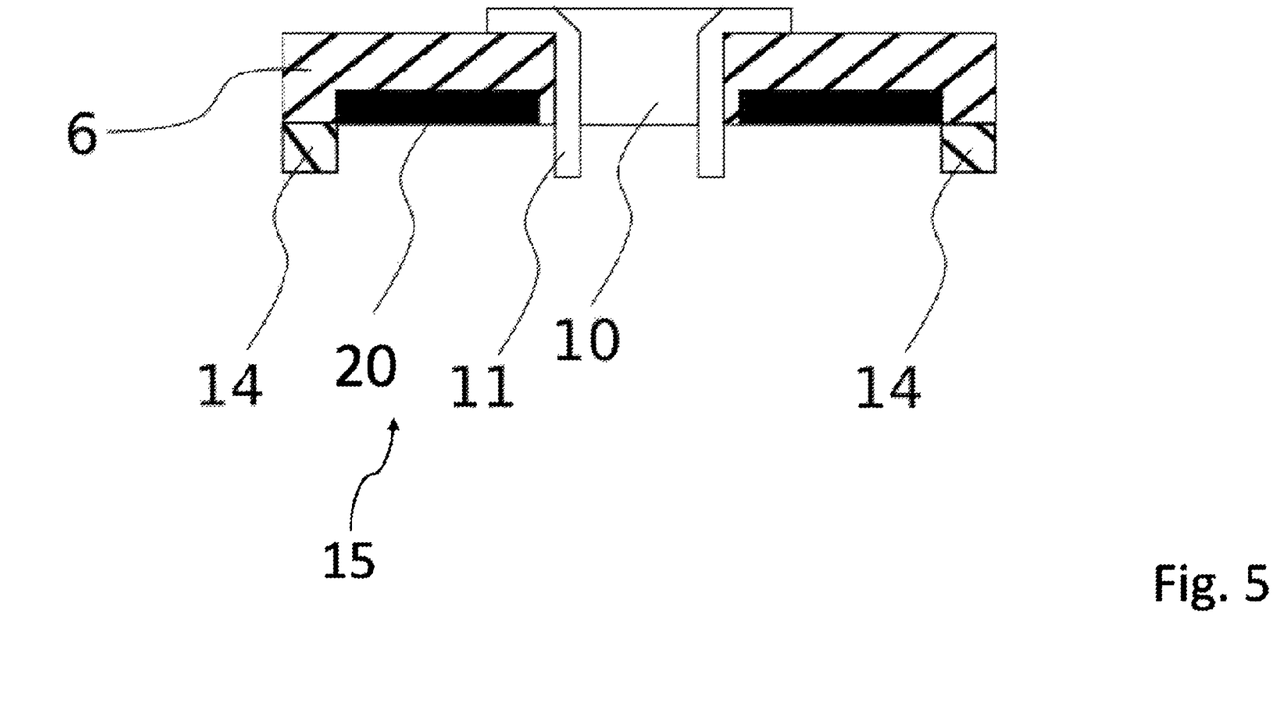
FIG. 5 shows a schematic illustration of an electrode body embedded in a carrier material, in a side view.

FIG. 5 shows a side view of the electrode body 20 embedded in a carrier material 6. It will be seen that the electrode body 20 has a continuous fastening opening 10, wherein an insulating material sleeve 11 is arranged in the fastening opening 10, and wherein the electrode body 20 can be fastened to a bone structure or other type of tissue structure of the living being via the insulating material sleeve 11 by means of a fastening element (not shown). It is clear that the carrier material 6 has a first circumferential sealing lip 14 on a contacting side 15 of the electrode body 20. The circumferential sealing lip 14 can be formed in one piece from the same material as the carrier material 6. In this way, despite unevenness, the electrode body 20 can be fastened at the implantation site without causing deformations of the electrode body 20. It is also conceivable here that the circumferential sealing lip 14 protrudes partially beyond the electrode body 20, thereby permitting improved fixing of the electrode body 20 in the carrier material 6. It will also be noted that the electrode body 20 is exposed on the contacting side 15 and is covered in an insulated manner by the carrier material 6 on the other side. The electrode body 20 is thus embedded in the carrier material 6. This permits efficient insulation of the electrode body 20 to the outside and at the same time ensures the generation of a desired electrical field in a body region toward the contacting side 15. It is also conceivable that the insulating material sleeve 11 has a second circumferential sealing lip (not shown), which promotes this effect still further.

Figure 6:
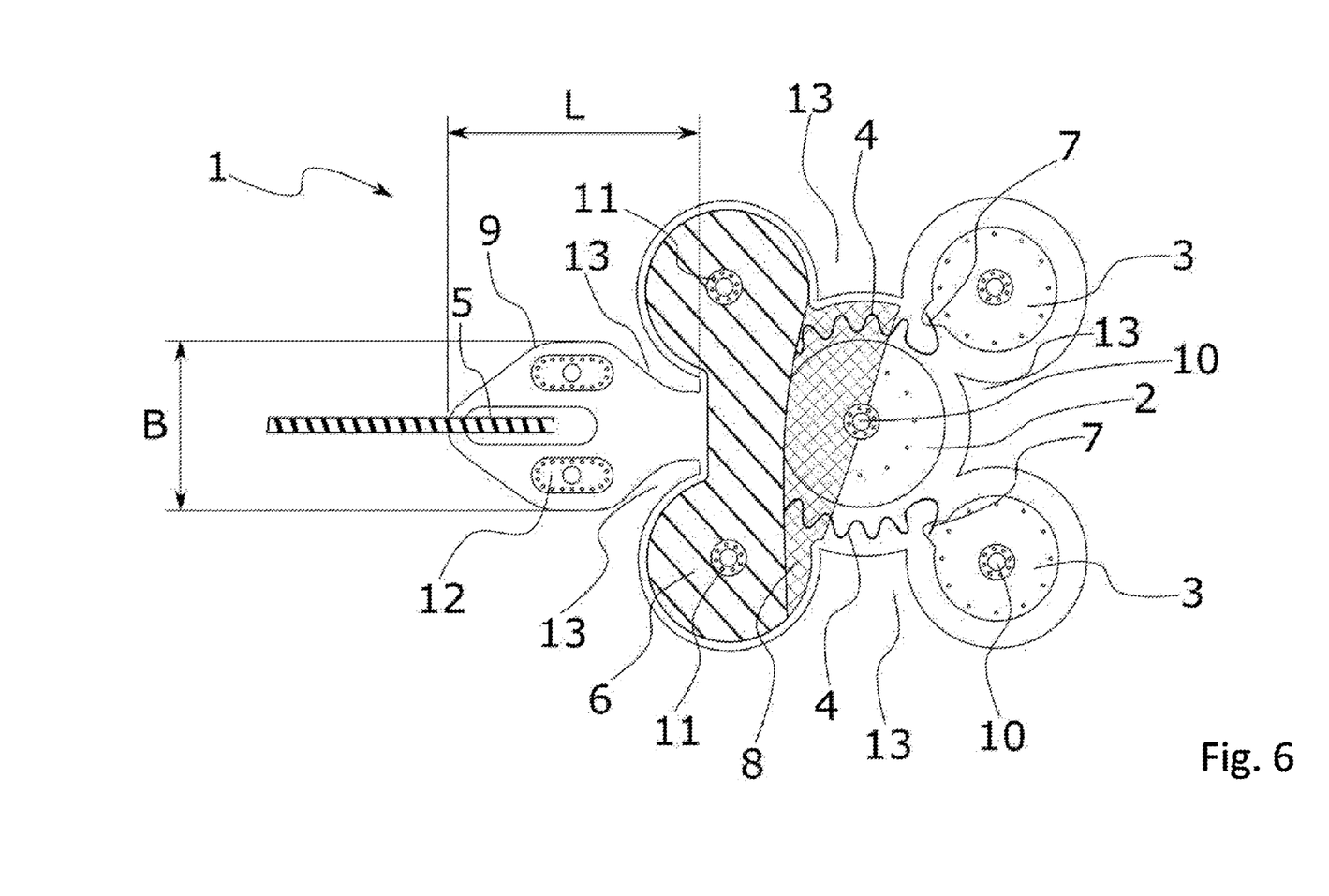
FIG. 6 shows a schematic illustration of an electrode assembly, in a plan view.

FIG. 6 shows a schematic illustration of an electrode assembly 1 in a plan view. For clarity, part of the electrode assembly 1 is cut away, revealing different layers of the electrode assembly 1. The electrode assembly 1 has a primary electrode 2, wherein the primary electrode 2 is surrounded by four secondary electrodes 3. The secondary electrodes 3 are arranged here on a common circular path around the primary electrode 2. The primary electrode 2 and the secondary electrodes 3 are each connected via a respective electrical conductor 4 to an attachment element 5, wherein the attachment element 5 is designed for attachment to an energy source 21. The primary and secondary electrodes 2, 3 can advantageously have further features of the above-described electrode body 20.

It is clear that the components (primary electrode 2, secondary electrodes 3, electrical conductors 4 and attachment element 5) are arranged on a carrier material 6. The carrier material 6 can be made of a silicone, for example. However, it is also conceivable to use other materials that satisfy the required properties (biocompatibility, flexibility, electrical insulation, etc.). It is clear that the primary electrode 2 and the secondary electrodes 3 and also the electrical conductors 4 are embedded in the carrier material 6. It is also clear that the electrical conductors 4 of the rear secondary electrodes 3 farther away from the attachment element 5 are arranged in a meandering shape around the primary electrode 1, wherein the meandering arrangement extends on a curved path around the primary electrode 2. In this way, it is possible to reduce the load on the electrical conductors 4 and hence also lessen the chance of failure of the secondary electrodes 3. The electrical conductors 4 are connected to the secondary electrodes 3 via a connection site, wherein the connection site is a tangential conductor connection point 7. The electrical conductor 4 can here be soldered or welded onto the secondary electrode 3, it being advantageous if the connection site is sealed off from external influences, for example with an epoxy resin.

A reinforcing element 8 in the form of a surgical net is arranged on the electrode assembly 1, wherein the reinforcing element 8 is drawn in between the outer layers of the carrier material. The reinforcing element 8 is here arranged between the primary electrode 2 and the secondary electrodes 3 in order to improve the tear resistance.

It will be seen that the attachment element 5 is arranged on a contacting portion 9, wherein the contacting portion 9 protrudes laterally from the electrode assembly 1 and has a greater length L than width B. The elongate design of the contacting portion 9 has the advantage that the attachment element 5 is decoupled from the primary electrode 2 and the secondary electrodes 3, wherein forces acting on the contacting portion 9 are compensated along the length L of the contacting portion 9 to such an extent that these forces are transmitted only weakly, or not at all, to the electrode assembly 1. In order to ensure the flexibility of the contacting portion 9, it may be advantageous if the reinforcing element 8 is not arranged on the contacting portion 9 and extends only as far as the transition region to the contacting portion 9 or, like a kink protection, extends into the contacting portion 9 while gradually decreasing in size.

The electrode assembly 1 is designed to be implanted, for example, between the scalp and skull of a living being. The primary electrode 2 and the secondary electrodes 3 have fastening openings 10, wherein an insulating material sleeve 11 is inserted into each fastening opening 10. The electrode assembly 1 can then be fastened to the skull of the living being via fastening elements, for example via screws, through the insulating material sleeve 11. The insulating material sleeve 11 here prevents a situation in which an excessive torque is transmitted to the primary electrode 2 or the secondary electrode 3 and thus damages these. Moreover, an undesired current flow between the electrodes (primary electrode 2 and secondary electrodes 3) and the fastening element is avoided. The insulating material sleeve 11 can be made, for example, from a polyether ether ketone. By fastening the electrode assembly 1 by way of fastening openings 10 on the respective electrodes (primary electrode 2 and secondary electrodes 3), it is possible to ensure an exact position of the electrodes, which can generate a desired electrical field in the target region. It will also be seen that, on the contacting portion 9, two fastening elements 12 are arranged for fastening to the living being by screws. The contacting portion 9 can be fastened to the skull of the living being by the fastening elements 12.

It is clear that the electrode assembly 1 has a clearance 13 in each case between the secondary electrodes 3. The clearances 13 increase the flexibility of the electrode assembly 1, more particularly in the region of the secondary electrodes 3. Since the bone of a living being is not generally flat, but the electrodes (primary electrode 2 and secondary electrodes 3) have to be positioned exactly on the bone, it is advantageous if the flexibility of the electrode assembly 1 is suitably great to ensure that the electrodes 2, 3 can be fastened suitably close to the bone and the electrode assembly 1 can conform well to the shape of the bone.

Figure 7:
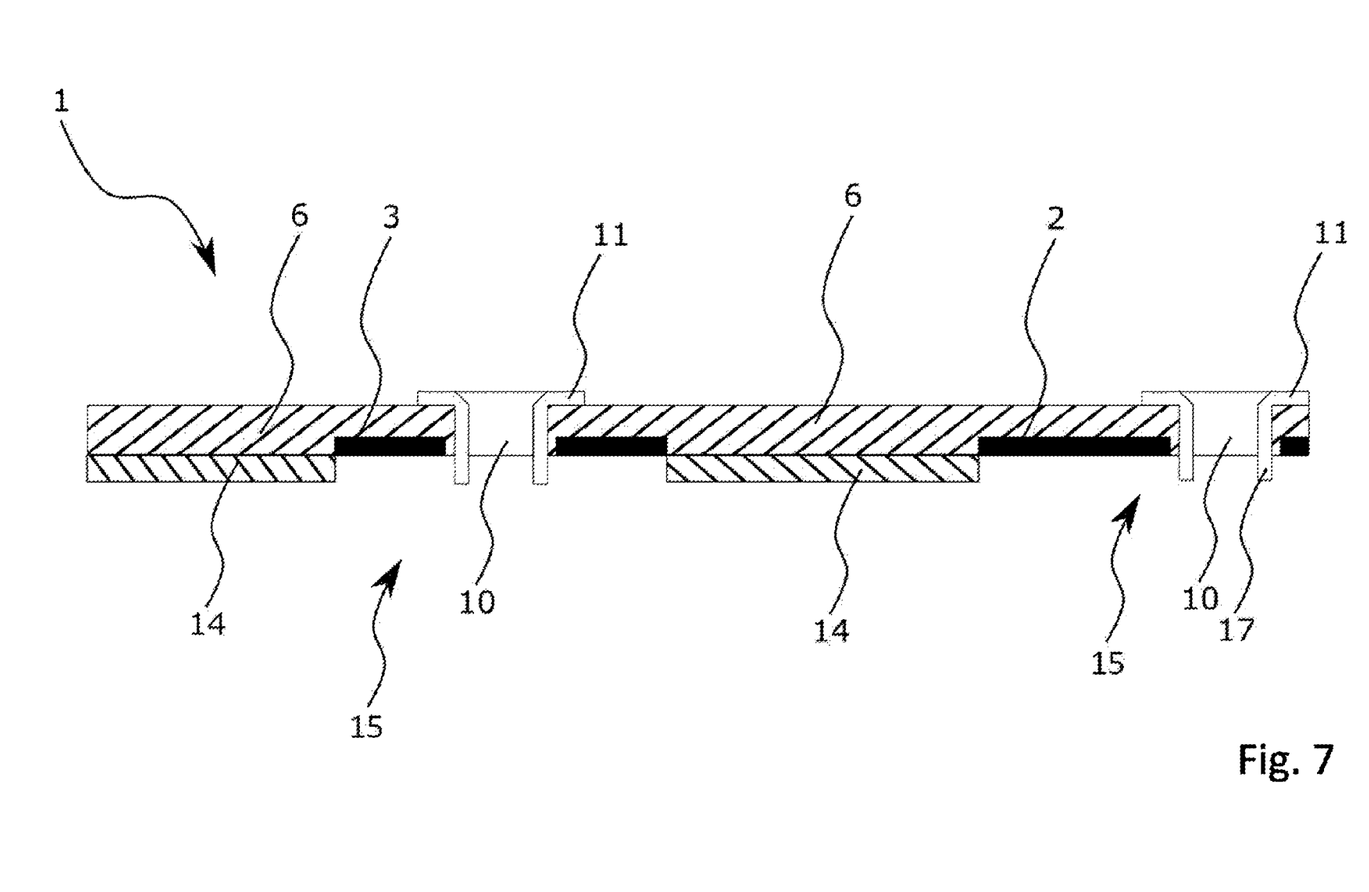
FIG. 7 shows a schematic illustration of an electrode assembly with electrodes embedded in a carrier material, in a side view.

FIG. 7 shows a schematic illustration of a primary electrode 2 and of a secondary electrode 3 in the carrier material 6, in a side view. It will be seen that the primary electrode 2 and the secondary electrode 3 each have a continuous fastening opening 10, wherein an insulating material sleeve 11 is arranged in the fastening opening 10, and wherein the electrode assembly 1 can be fastened to a bone or tissue structure of a living being via the insulating material sleeve 11 by means of fastening elements.

It is clear that the carrier material 6 has a first circumferential sealing lip 14 on the exposed contacting side 15 of the secondary electrodes 3. The circumferential sealing lip 14 can be formed in one piece from the same material as the carrier material 6. In this way, despite unevenness, the electrode assembly 1 can be fastened at the implantation site without causing deformations of the secondary electrodes 3. It is also conceivable here that the circumferential sealing lip 14 protrudes partially beyond the secondary electrode 3, thereby permitting improved fixing of the secondary electrode 3 in the carrier material 6. It will also be noted that the secondary electrodes 3 are exposed on the contacting side 15 and are covered in an insulated manner by the carrier material 6 on the other side. The secondary electrodes 3 are thus embedded in the carrier material 6. This permits efficient insulation of the secondary electrodes 3 to the outside and at the same time ensures the generation of a desired electrical field in a body region toward the contacting side 15. It is also conceivable that the insulating material sleeve 11 has a second circumferential sealing lip 17, which promotes this effect still further. It is advantageous if all the electrodes of the electrode assembly 1 have these configurations.

Figure 8:
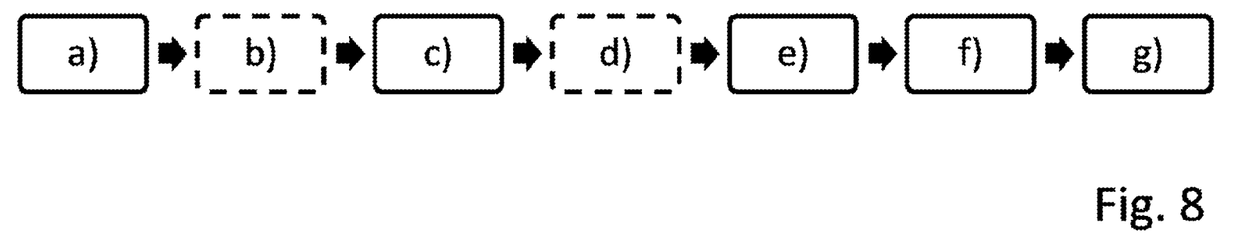
FIG. 8 shows a schematic illustration of a method for producing an electrode assembly.

FIG. 8 shows schematically a method for producing an electrode assembly for electrical stimulation of tissue of a living being, more particularly for producing an electrode assembly 1 in accordance with the features described above.

In a method step a), electrode bodies 20 are produced from a film of an electrode material of suitable thickness, e.g. by punching out or cutting out, e.g. with a laser. In an optional method step b), a surface coating and/or a structuring of the surface is applied on at least one part of the electrode surface. In a method step c), an electrical conductor 4 is mounted on each electrode body 20. In an optional method step d), an epoxy resin or another electrical insulator is applied to the connection site. In a method step e), a mold of the electrode assembly 1 is cast from the carrier material 6. In a method step f), the electrode body 20 and optionally the electrical conductor 40 and optionally the reinforcing element 8 are embedded. In a method step g), an electrical conductor 4 is connected to the contacting portion 9 of the electrode assembly 1.

Figure 9:
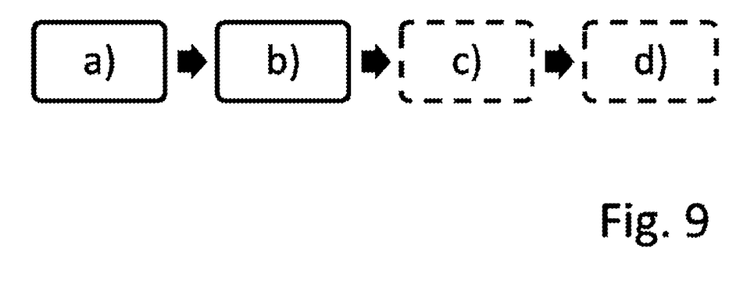
FIG. 9 shows a schematic illustration of a further method for producing an electrode assembly.

FIG. 9 shows schematically a further method for producing an electrode assembly 1 for electrical stimulation of tissue of a living being, more particularly for producing an electrode assembly 1 in accordance with the features described above. In a method step a), a carrier material 6 is made available. In a method step b), one or more electrode bodies 20 are generated on the carrier material 6 by a chemical vapor deposition process and/or by electrolytic deposition. In an optional method step c), a surface coating and/or structuring of a surface is applied on at least one part of the electrode surface. In an optional method step d), the carrier material 6 is embedded in a further insulating carrier material.

The figures are to be understood as a possible illustrative embodiment. Other forms of the teaching according to the invention are also conceivable.

Furthermore, the elements of the illustrative embodiment are not linked inseparably to one another, and therefore, for example, the implementation of the invention is not dependent on the specifically described elements of the illustrative embodiment. It is thus always conceivable, for example, for there to be variability in the number or positioning of the individual elements, for example of the primary electrode 2, the secondary electrodes 3, the clearances 13 and/or the recesses 16.

The invention claimed is:

1. An electrode assembly for neurostimulation by electrical stimulation of tissue of a living being, comprising:
    a conductive electrode body configured to be arranged between the skull and the scalp of a living being, wherein the conductive electrode body extends to an edge and includes
        a stimulation surface configured to be brought into contact with a tissue of the living being between the skull and the scalp when the conductive electrode body is arranged between the skull and the scalp, and in said contact to generate, responsive to receipt of alternating-current pulses and/or direct-current pulses, the electrical stimulation of the tissue, and
        recesses, distributed over a perimeter area inward of the edge of the conductive electrode body, wherein the recesses are configured to receive a carrier material, for fixing the conductive electrode body in the carrier material.

2. The electrode assembly as claimed in claim 1, further comprising:
    a conductor connection point, configured for electrically conductive connecting an electrical conductor to the conductive electrode body, by solder, adhesive bond, weld or another connection technique, to for electrically connecting the conductive electrode body to an electrical device or to another electrode body.

3. The electrode assembly as claimed in claim 2, wherein the conductor connection point is configured as a tangential or right-angled conductor connection point.

4. The electrode assembly as claimed in claim 2, further comprising an electrical conductor element having one end electrically connected to the conductor connection point and an another end electrically connected to an electrical device or to another electrode body wherein the electrical conductor element is configured with a meandering form.

5. The electrode assembly as claimed in claim 1, further comprising a fixing structure configured to fix the conductive electrode body to the tissue, wherein the fixing structure includes an insulator element, which is configured to insulate a mechanical fastening element from the conductive electrode body.

6. The electrode assembly as claimed in claim 5, wherein the conductive electrode body includes a fastening opening configured for the the mechanical fastening element to pass through to fix the conductive electrode body to the tissue of the living being.

7. The electrode assembly as claimed in claim 6, wherein the insulator element comprises an insulating material sleeve that is arranged in the fastening opening.

8. The electrode assembly as claimed in claim 7, wherein the insulating material sleeve comprises an at least partially circumferential sealing lip.

9. An electrode according to claim 7, wherein the insulating material sleeve comprises at least two holes, the at least two holes configured to accommodate, respectively, a passing of a surgical thread into and from a tissue under the conductive electrode body.

* * * * *